United States Patent
Pfabe et al.

(10) Patent No.: US 9,498,200 B2
(45) Date of Patent: Nov. 22, 2016

(54) METHOD OF RETRACTING BODY TISSUE DURING SURGERY

(71) Applicant: SPINE WAVE, INC., Shelton, CT (US)

(72) Inventors: Hubert W. Pfabe, East Longmeadow, MA (US); Thomas R. Rainey, Norwalk, CT (US)

(73) Assignee: SPINE WAVE, INC., Shelton, CT (US)

( * ) Notice: Subject to any disclaimer, the term of this patent is extended or adjusted under 35 U.S.C. 154(b) by 182 days.

(21) Appl. No.: 14/277,511

(22) Filed: May 14, 2014

(65) Prior Publication Data

US 2014/0336468 A1    Nov. 13, 2014

Related U.S. Application Data

(63) Continuation of application No. 13/891,697, filed on May 10, 2013, now Pat. No. 8,727,975.

(51) Int. Cl.
| | | |
|---|---|---|
| *A61B 1/32* | (2006.01) | |
| *A61B 17/02* | (2006.01) | |
| *A61B 17/29* | (2006.01) | |
| *A61B 17/00* | (2006.01) | |

(52) U.S. Cl.
CPC ......... *A61B 17/025* (2013.01); *A61B 17/0206* (2013.01); *A61B 17/0293* (2013.01); *A61B 2017/00367* (2013.01); *A61B 2017/0256* (2013.01); *A61B 2017/0262* (2013.01); *A61B 2017/2923* (2013.01)

(58) Field of Classification Search
CPC  A61B 17/02;  A61B 1/32;  A61B 2017/0256; A61B 19/5202;  A61B 17/0206

USPC .................................................. 600/227–234
See application file for complete search history.

(56) References Cited

U.S. PATENT DOCUMENTS

| | | |
|---|---|---|
| 475,975 A | 5/1892 | Clough |
| 497,064 A | 5/1893 | Van Meter |
| 2,083,573 A | 6/1937 | Morgan |

(Continued)

FOREIGN PATENT DOCUMENTS

| | | |
|---|---|---|
| FR | 542744 | 8/1922 |
| WO | 0103586 A1 | 1/2001 |
| WO | 2008039427 A2 | 4/2008 |

OTHER PUBLICATIONS

FISSO, Articulated arm for surgical applications with quick central fixation, dated Oct. 2007 (6 pages).

*Primary Examiner* — Mary Hoffman
*Assistant Examiner* — Tara R Carter
(74) *Attorney, Agent, or Firm* — Hoffmann & Baron, LLP

(57) ABSTRACT

A retractor for use in spinal surgery comprises a frame including a ring member defining a generally central interior space. A plurality of blades is releasably supported respectively to slidable arms each supported on the ring member for individual translational movement relative to the ring member. The blades define an initial substantially enclosed opening that is expandable for use in a surgical procedure. A clutch mechanism supported on the ring member is associated with each arm to individually selectively engage each such arm with a rotatable main gear such that upon rotation of the main gear by a single actuator any one, all or any desired combination of arms may be translated relative to the ring member to move the blades and expand the opening in one or more selected desired directions.

11 Claims, 17 Drawing Sheets

(56) References Cited

U.S. PATENT DOCUMENTS

| | | |
|---|---|---|
| 3,522,799 A | 8/1970 | Gauthier |
| 3,749,088 A | 7/1973 | Kohlmann |
| 3,965,890 A | 6/1976 | Gauthier |
| 4,130,113 A | 12/1978 | Graham |
| 5,520,610 A | 5/1996 | Giglio et al. |
| 5,947,896 A | 9/1999 | Sherts et al. |
| 5,957,902 A | 9/1999 | Teves |
| 6,074,343 A | 6/2000 | Nathanson et al. |
| 6,102,853 A | 8/2000 | Scirica et al. |
| 6,402,780 B2 | 6/2002 | Williamson, IV et al. |
| 6,616,605 B2 | 9/2003 | Wright et al. |
| 6,712,795 B1 | 3/2004 | Cohen |
| 7,344,495 B2 | 3/2008 | Ravikumar et al. |
| 7,722,570 B2 | 5/2010 | Almond et al. |
| 7,758,501 B2 | 7/2010 | Frasier et al. |
| 7,985,179 B2 | 7/2011 | Gephart et al. |
| 8,062,217 B2 | 11/2011 | Boucher et al. |
| 8,251,902 B2 | 8/2012 | Parker et al. |
| 8,355,780 B2 | 1/2013 | Miles et al. |
| 8,409,089 B2 | 4/2013 | Michaeli et al. |
| 2004/0087833 A1 | 5/2004 | Bauer et al. |
| 2005/0149035 A1* | 7/2005 | Pimenta et al. ............... 606/86 |
| 2005/0159651 A1* | 7/2005 | Raymond et al. ............ 600/213 |
| 2005/0165281 A1 | 7/2005 | Ravikumar et al. |
| 2006/0135852 A1 | 6/2006 | Koros et al. |
| 2007/0010716 A1 | 1/2007 | Malandain et al. |
| 2007/0208228 A1 | 9/2007 | Pavento et al. |
| 2007/0213597 A1* | 9/2007 | Wooster ....................... 600/234 |
| 2007/0238932 A1 | 10/2007 | Jones et al. |
| 2008/0319268 A1 | 12/2008 | Michaeli et al. |
| 2011/0004067 A1 | 1/2011 | Marchek et al. |
| 2011/0301421 A1 | 12/2011 | Michaeli et al. |
| 2012/0232349 A1 | 9/2012 | Perrow |
| 2013/0261402 A1 | 10/2013 | Hawkins et al. |
| 2014/0114138 A1 | 4/2014 | Fedorov et al. |

\* cited by examiner

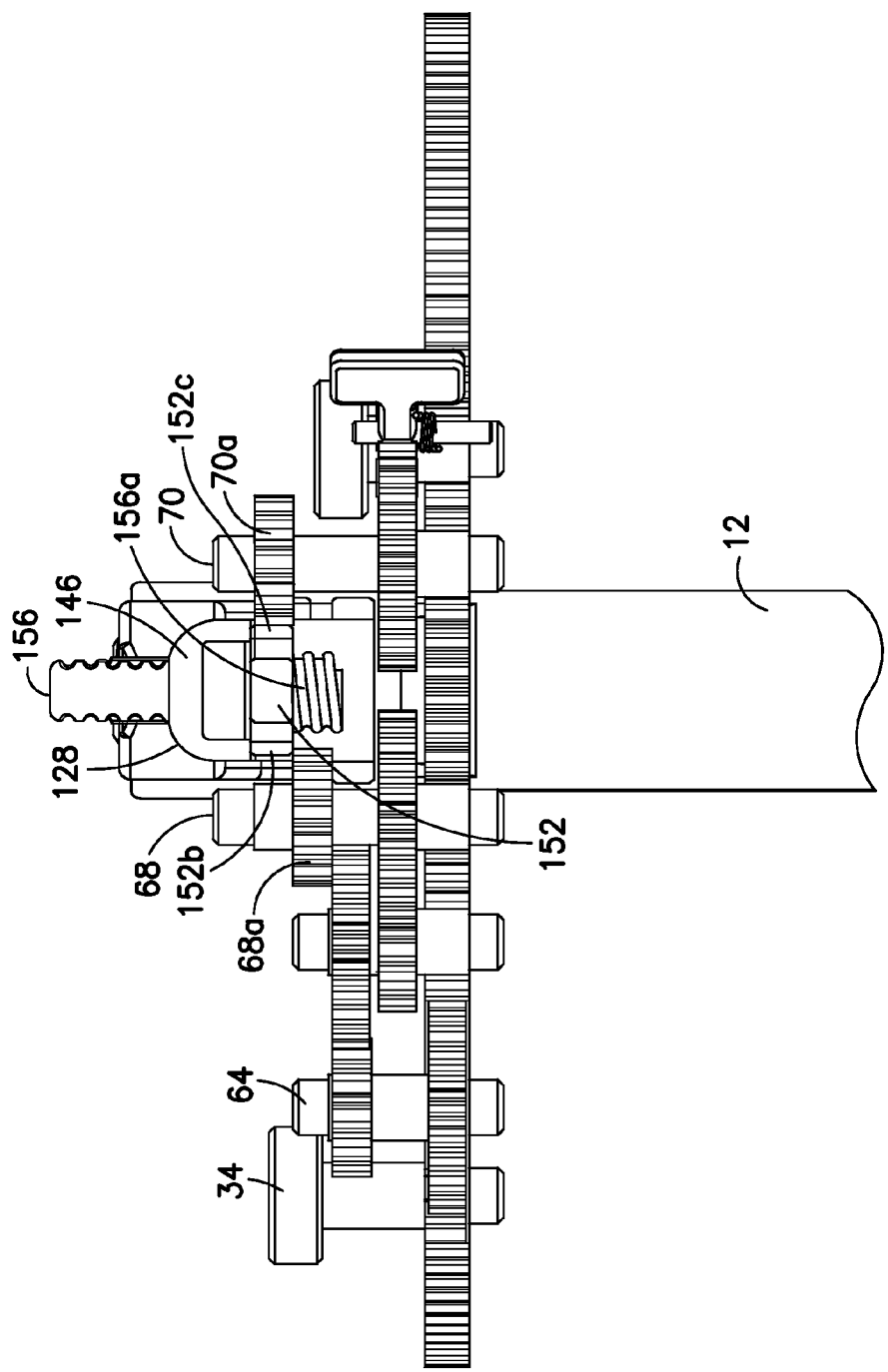

METHOD OF RETRACTING BODY TISSUE DURING SURGERY

CROSS-REFERENCE TO RELATED APPLICATION

This application is a continuation of U.S. application Ser. No. 13/891,697, filed May 10, 2013, now U.S. Pat. No. 8,727,975, the entire contents of which are incorporated by reference herein.

FIELD OF THE INVENTION

The subject invention relates generally to the field of retractors for retracting bodily tissue during surgery and more particularly to a retractor for use in spinal surgery.

BACKGROUND OF THE INVENTION

Retractors are commonly used in surgical procedures to separate and expand an incision to access the surgical site and to minimize trauma to the patient. While there are many styles, shapes and sizes of retractors, the typical retractor used in spinal surgery comprises a plurality of retractable blades, which may include two to four or more blades that are introduced through the surgical incision to form a protected corridor to the surgical site. Various mechanisms are provided to move one or more blades in different directions so as to expand the incision and to hold the blades in the expanded position. One factor in the surgeon's decision as to the type of retractor used is the control of the blade movement. Blades are often configured to not only expand outwardly so as to expand the corridor but also to pivot or toe at their distal ends so as to increase the opening of the corridor adjacent the surgical site. In addition, the size of the retractor is often of consequence, with the surgeon typically seeking to minimize the overall footprint of the retractor for ease of handling, placement and use during surgery.

Accordingly, it is desirable to provide a retractor that not only satisfies these needs but also provides additional flexibility in the use, adjustability and control of the movement of the blades during spinal surgery.

SUMMARY OF THE INVENTION

It is an object of the invention to provide an improved retractor for use during surgery, particularly spinal surgery.

DESCRIPTION OF THE FIGURES

FIG. 17 is a further partial side view of the retractor gearing mechanism shown in FIG. 16 with the switch in the second position of FIG. 15.

DESCRIPTION OF THE EMBODIMENTS

Figure 1:
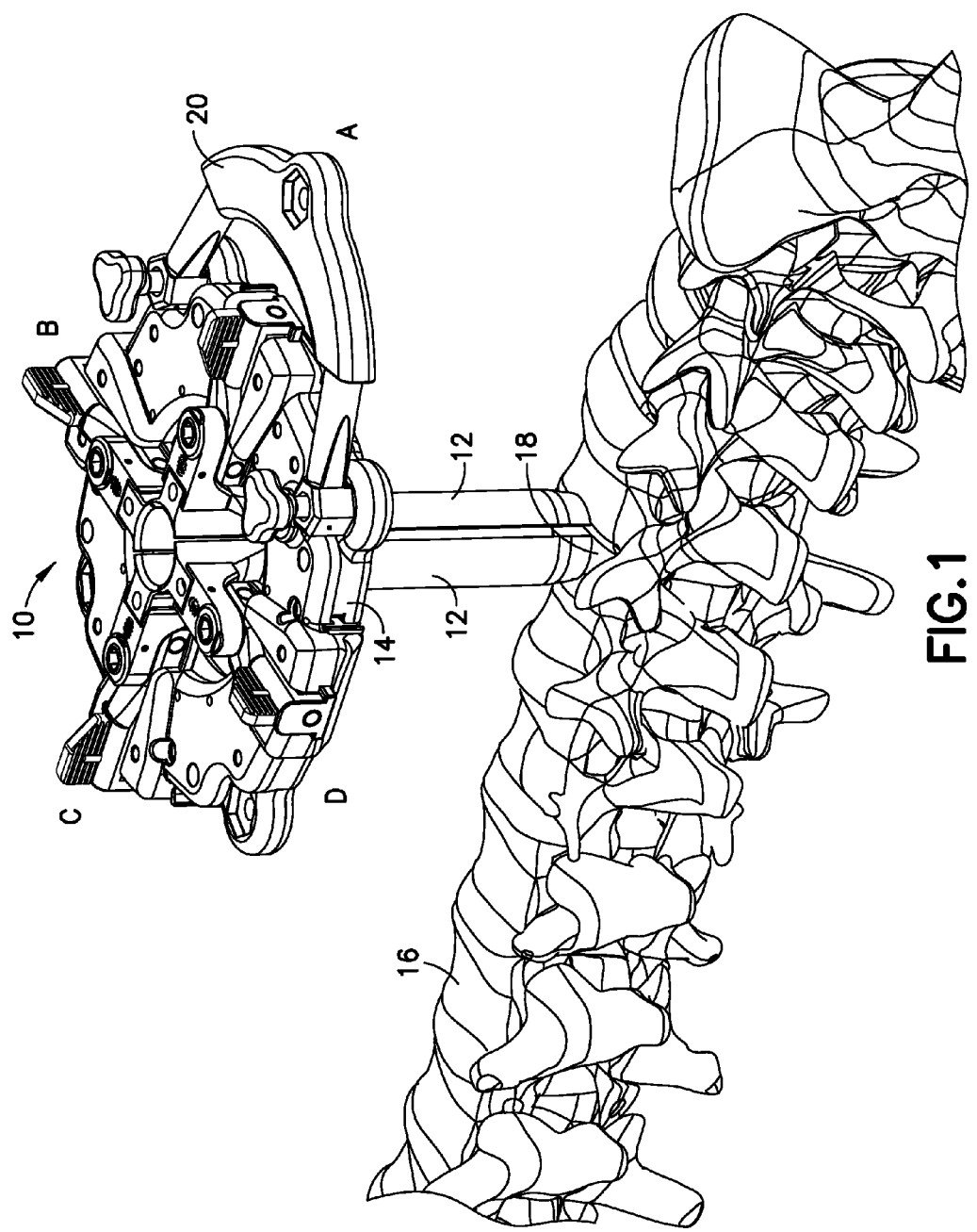
FIG. 1 is a top perspective of a retractor in accordance with an embodiment of the present invention for use during spinal surgery.

For the purposes of promoting and understanding the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, a retractor 10 is shown in a particular arrangement for use in spinal surgery. In the arrangement shown, retractor 10 comprises four blades 12 each being identical and spaced radially substantially equally at approximately 90° relative to each other. The blades 12 project substantially transversely downwardly from a frame 14 toward a human spine 16 to define an expandable minimally invasive corridor through which a surgical procedure including the implantation of an implant into an intradiscal space 18 of the spine 16 may be performed. As will be described, the blades 12 are supported by the retractor 10 whereby one or all or any combination of blades 12 may be translated in a radial direction from a single source actuator to expand an incision through bodily tissue in a controlled manner.

In the spinal surgical procedure illustrated in FIG. 1 the use of the retractor 10 is from a direct lateral approach to the surgical site. The retractor 10 is oriented to define four quadrants A, B, C and D, with quadrant A being in the caudal direction, quadrant B being in the anterior direction, quadrant C being in the cephalad direction and quadrant D being in the posterior direction. The desired orientation may be maintained as will be further described by a bracket 20 suitably attached to the frame 14 of retractor 10 with the bracket 20 suitably connected to a rigid mounting arm connected to an operating table on which the patient is lying.

Figure 2:
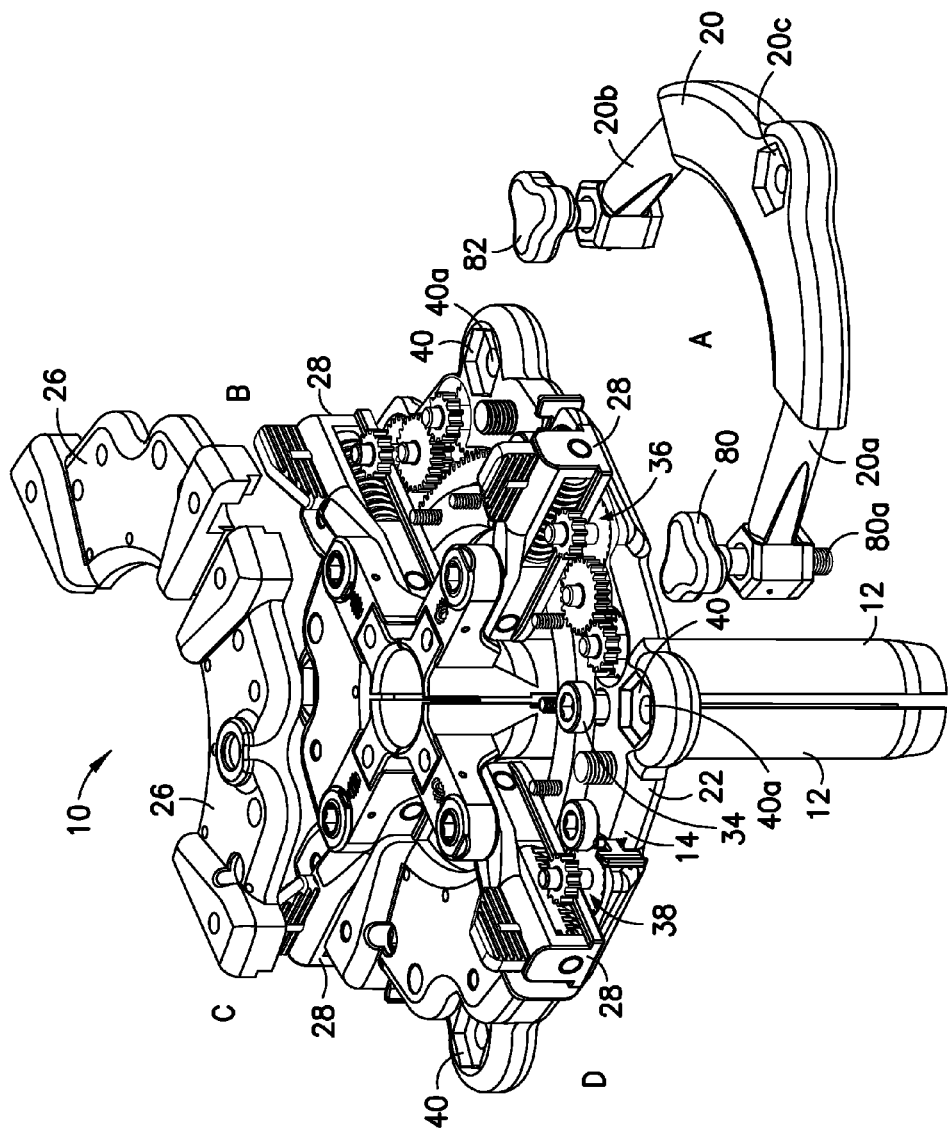
FIG. 2 is a partially exploded top perspective view of the retractor of FIG. 1.
Figure 3:
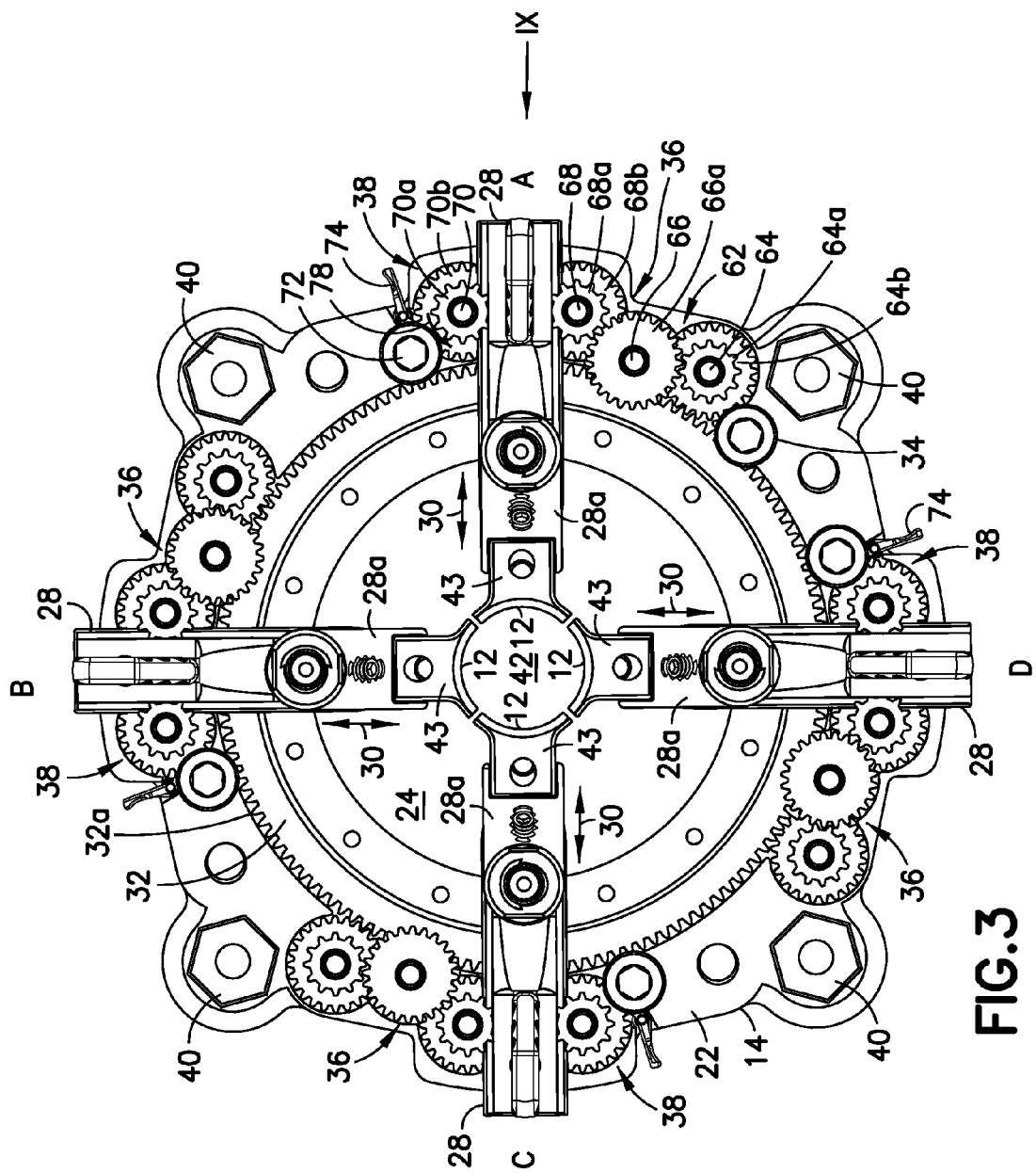
FIG. 3 is a top plan view of the retractor of FIG. 1 with the covers and the mounting bracket removed for clarity.

Turning now to FIGS. 2-3, further details of the retractor 10 are described. Frame 14 comprises a lower ring member 22 defining a generally central fully enclosed interior space 24. Frame 14 includes a cover 26 of substantially the same structure associated with each of the quadrants A, B, C and D each of which covers a gear mechanism for use in selectively translating the blades 12, as will be described. The ring member 22 supports four arms 28 one each at the quadrants A, B, C and D, each arm 28 supporting a blade 12 at a distal portion 28a thereof. The arms 28 are each radially individually translatable on the ring member 22 with the distal portions 28a and blades attached thereto being movable within the interior space 24 along the radial directions indicated by arrows 30 in FIG. 3.

Still referring to FIGS. 2-3, ring member 22 supports a transmission member defined by a main gear 32 for rotational movement relative to ring member 22 and thereby relative to each arm 28. Main gear 32 comprises a plurality of gear teeth 32a extending around the circumference of main gear 32. Ring member 22 supports an actuator 34 disposed in this particular arrangement between quadrants A and D. The lower portion of actuator 34 defines a drive gear 34a having gear teeth 34b (see FIG. 9) in engagement with teeth 32a on the main gear 32. The upper portion of actuator 34 defines a hex portion 34c configured for engagement with a suitable tool such as, for example, a tool with a T-handle (not shown) having a complementary hex portion. Rotation of the tool rotates actuator 34 and the drive gear 34a which in turn rotates main gear 32. Associated with each arm 28 and supported by ring member 22 in each of the quadrants A, B, C and D is a clutch mechanism 36 that is configured to selectively engage a selected arm 28 with the main gear 32, as will be detailed hereinbelow. Also associated with each arm 28 and supported by ring member 22 in each of the quadrants A, B, C and D is a locking mechanism 38 that cooperates with each arm 28 to allow translational movement of such arm 28 in only one direction and locking in the opposite direction, as will be described in further detail. Between each of the quadrants A, B, C and D ring member 22 is configured to have a mounting portion 40 by which the retractor 10 may be directly connected to the operating table by a mounting arm or to which bracket 20 may be connected for attachment to the mounting arm.

Figure 4:
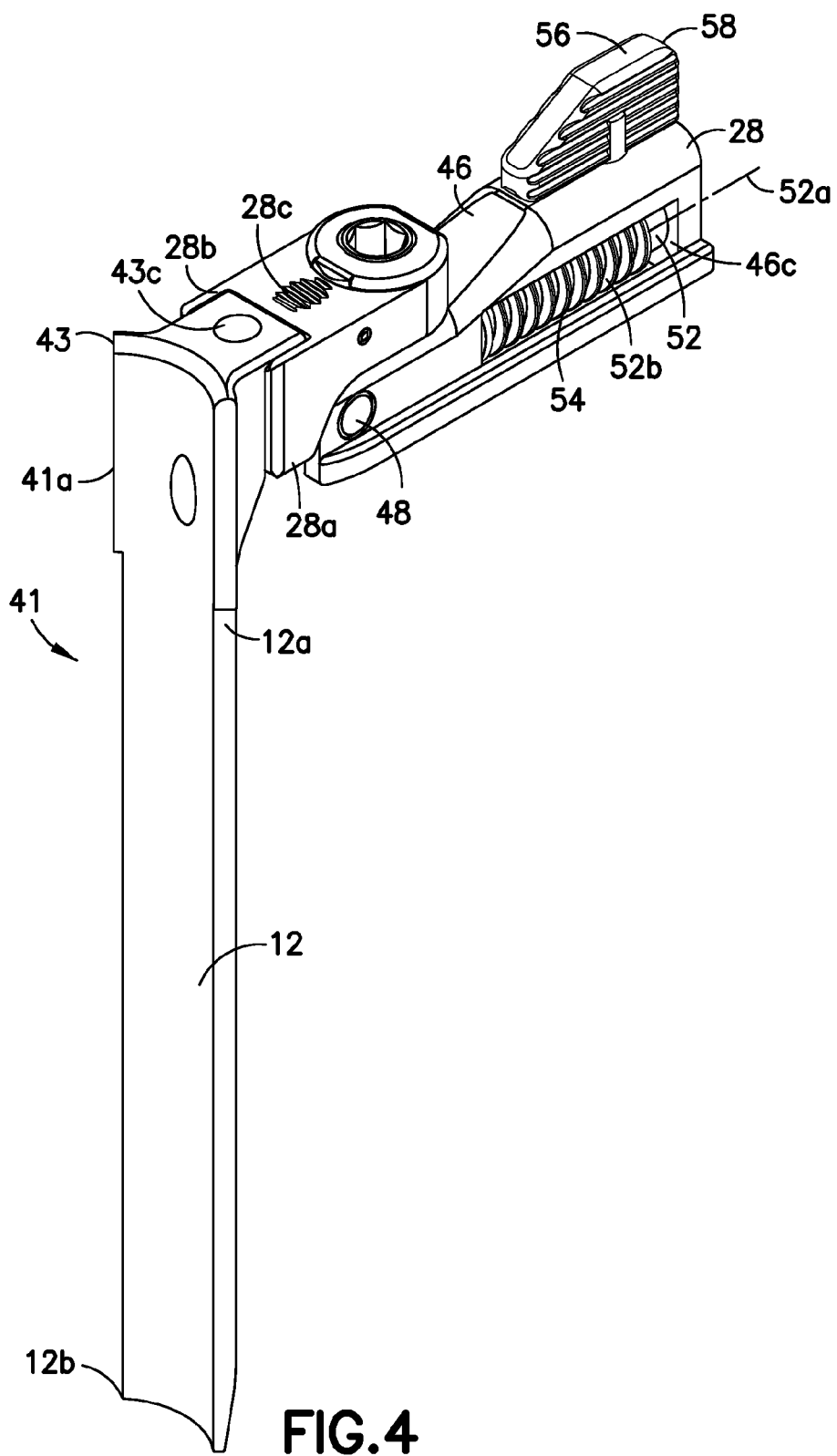
FIG. 4 is a top perspective view of one translatable arm of the retractor of FIG. 1 with a retractor member including a blade attached thereto with a switch being oriented in a first position.
Figure 5:
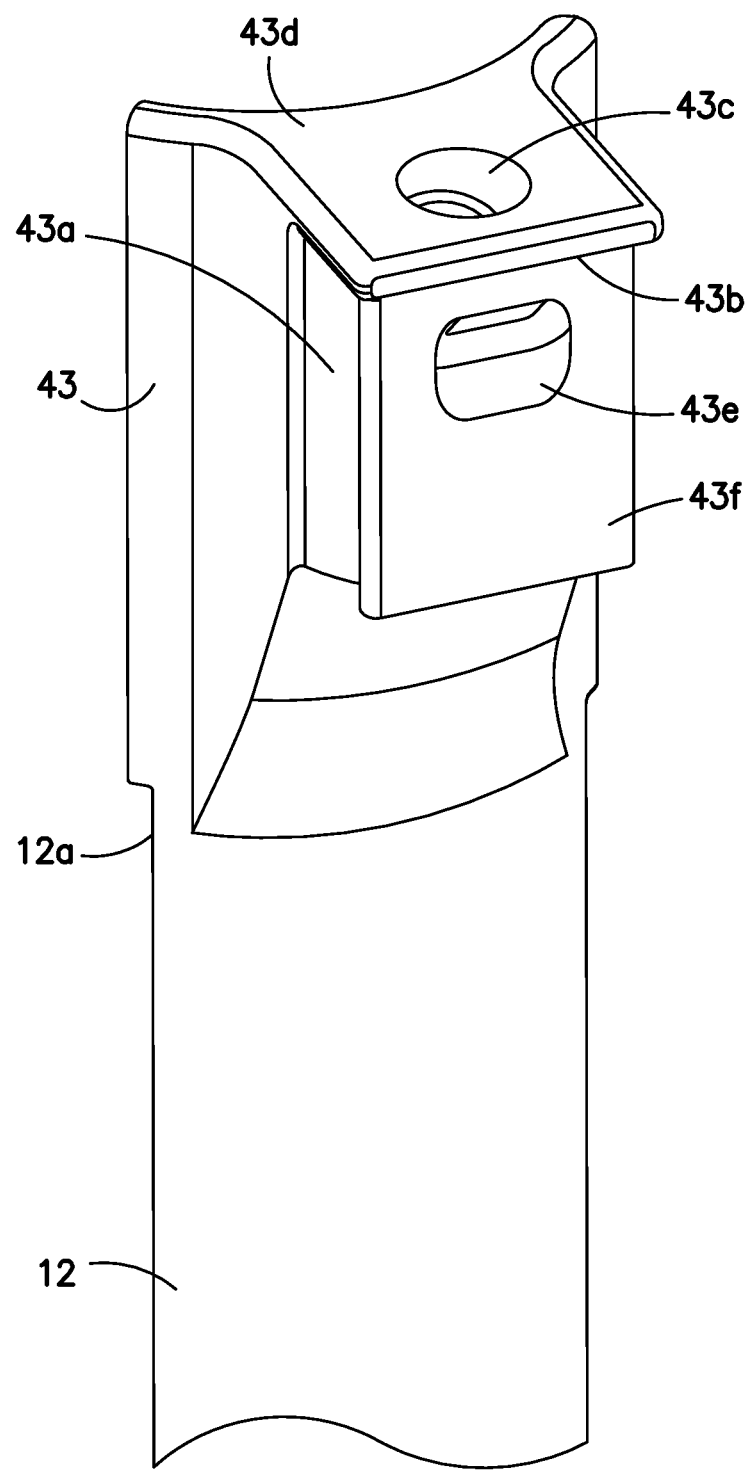
FIG. 5 is a partial top perspective rear view of the retractor member shown in FIG. 4.

Referring now to FIGS. 4-7 further details of the blades 12, the attachment to the arms 28 and a pivoting or toeing motion of the blades 12 are described. A retractor member 41 for releasable attachment to each housing 28 comprises blade 12 and a blade support 43. Blade support 43 is disposed at the proximal end 41a of retractor member 41. Each blade 12 is elongate and includes a proximal end 12a attached to blade support 43 and a distal end 12b. An outer surface 12c extending along the length of the blade 12 is configured to have a concave surface to form a quadrant of a surgical corridor formed by the four blades 12 having a substantially enclosed opening 42 as shown in FIG. 1. As illustrated in FIG. 5, blade support 43 includes a dovetail slot 43a that cooperates with a complementary dovetail slot 28b in distal portion 28a of arm 28 for releasably mounting retractor member 41 thereto. The blade support 43 includes a flange 43b which serves as a stop to properly seat retractor member 41 as the dovetail slots engage during insertion of retractor member 41 from above distal portion 28a. Blade support 43 may include an opening 43c extending obliquely through an upper surface 43d and opening through concave surface 12c. Opening 43c may be used for insertion of a light cable or other optical device to illuminate the opening 42 of the surgical corridor. The retractor member 41 with blade 12 is releasably secured by a set screw 44 threadedly received in a threaded opening 28c. The bottom of said screw 44 is received in a recess 43e formed in a side face 43f of the blade support 43.

Figure 6:
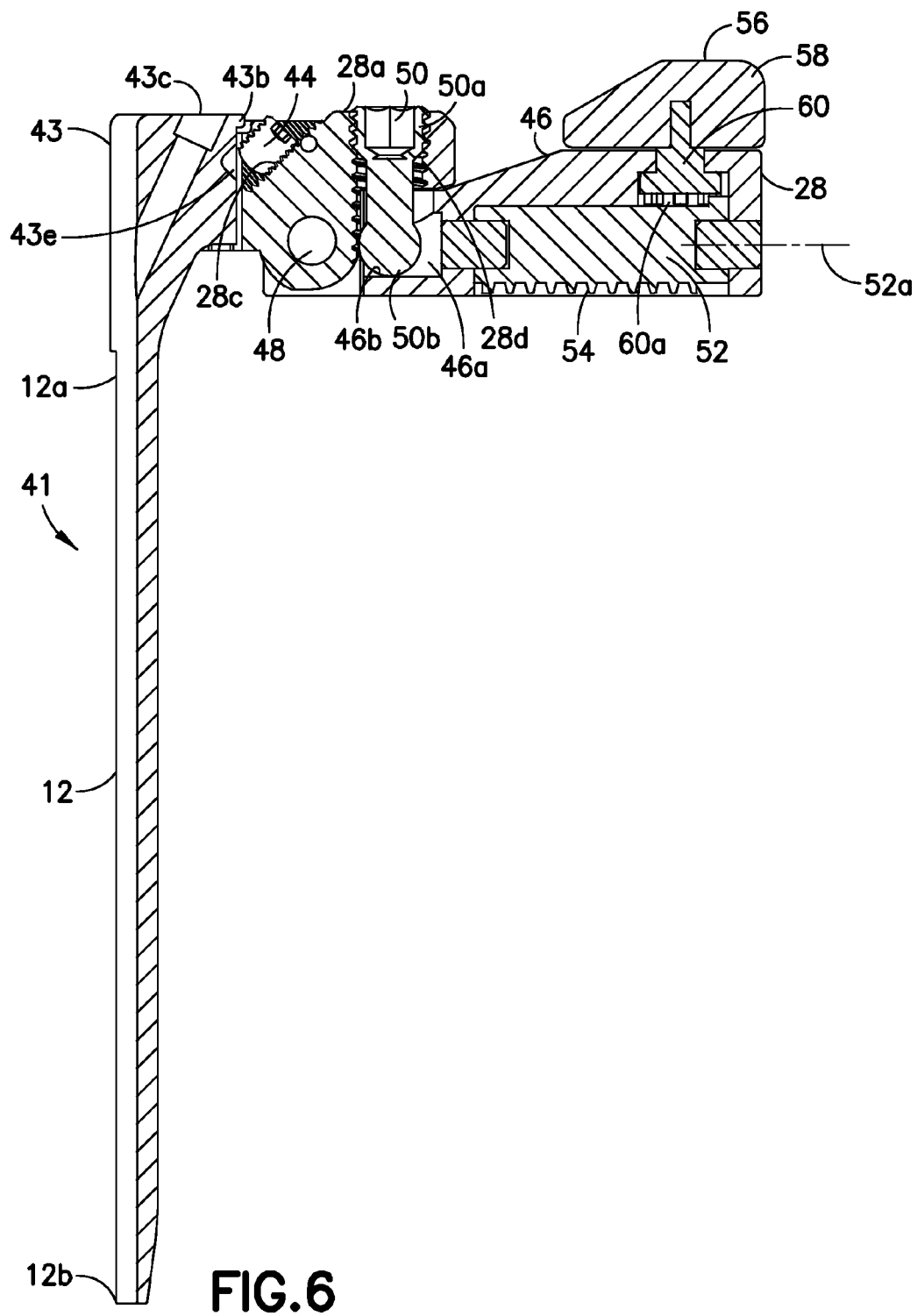
FIG. 6 is a longitudinal cross-sectional view of the arm and retractor member of FIG. 4.
Figure 7:
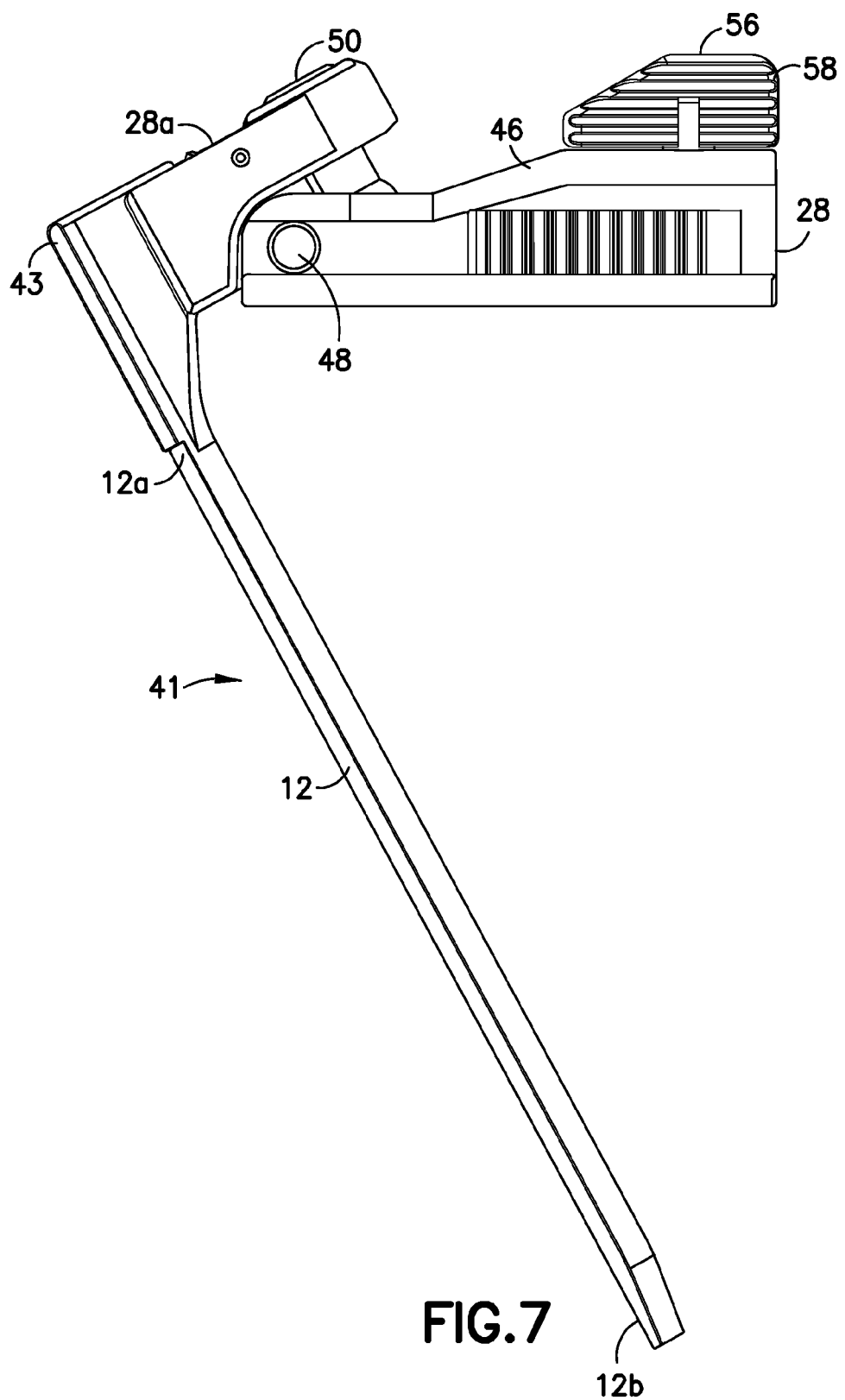
FIG. 7 is a side elevation view of the arm shown in FIG. 4 *with* the blade in a toed position.

With further reference to FIGS. 6-7, each arm 28 comprises a housing 46 to which the distal portion 28a is pivotally attached by a pivot pin 48. The distal portion 28a includes a threaded opening 28d for threadedly receiving therein a toeing screw 50 the upper portion 50a of which is threaded to engage the threads of threaded opening 28d. The lower portion is formed to have a generally spherical portion 50b that is movably situated in a housing cavity 46a. As toeing screw 50 is threaded into threaded opening 28d generally spherical portion 58b will contact surface 46b of the housing 46 causing the distal portion 28a of the arm 28 to pivot about pivot pin 48 as shown in FIG. 7. During the pivoting motion the generally spherical portion 50b will move within cavity 46a along surface 46b as the toeing motion continues. Retractor member 41 with blade 12 that is attached to distal portion 28a likewise pivots with the pivoting of distal portion 28a. Toeing movement up to about 30° may be achieved to further expand the opening 42 at the distal ends 12b of the blades adjacent the surgical site.

Figure 8:
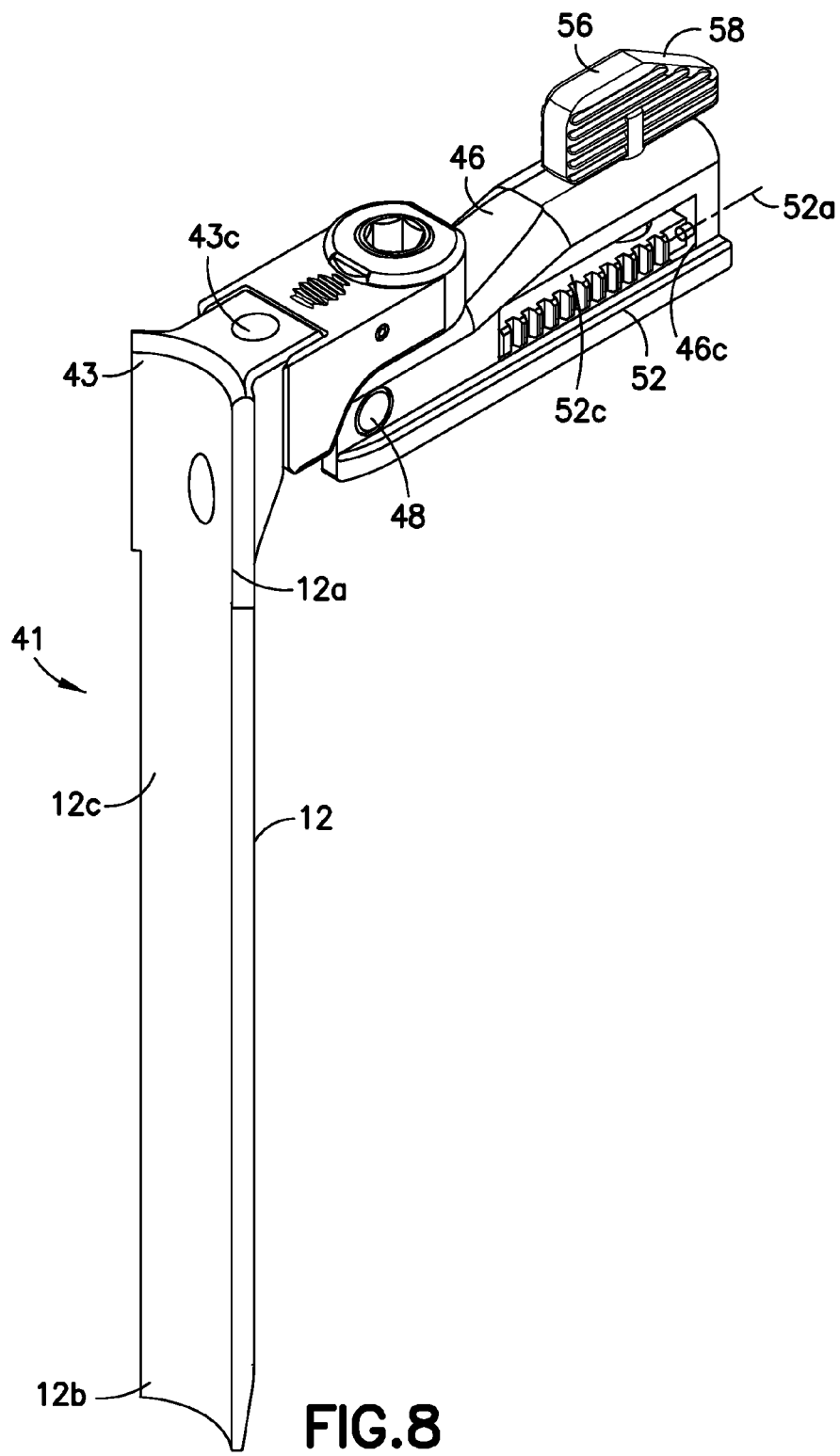
FIG. 8 is a top perspective view of the translatable arm and retractor member of FIG. 4 with the switch being oriented in a second position.
Figure 9:
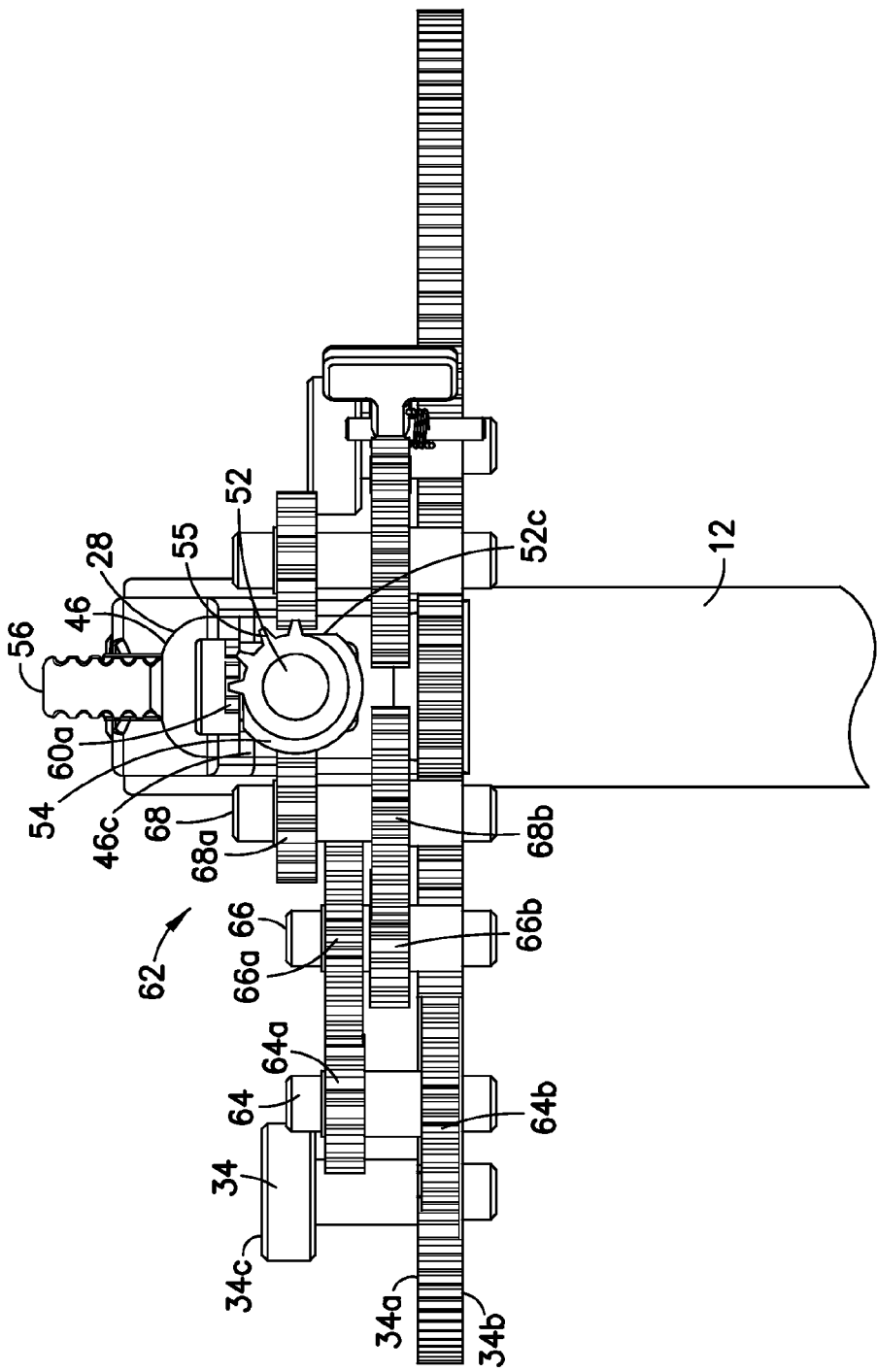
FIG. 9 is a partial side view of the retractor of FIG. 3 as viewed along the direction line IX in FIG. 3 with a portion of the retractor frame removed to reveal only the gearing mechanism in one quadrant of the retractor with the switch in the first position of FIG. 4.
Figure 10:
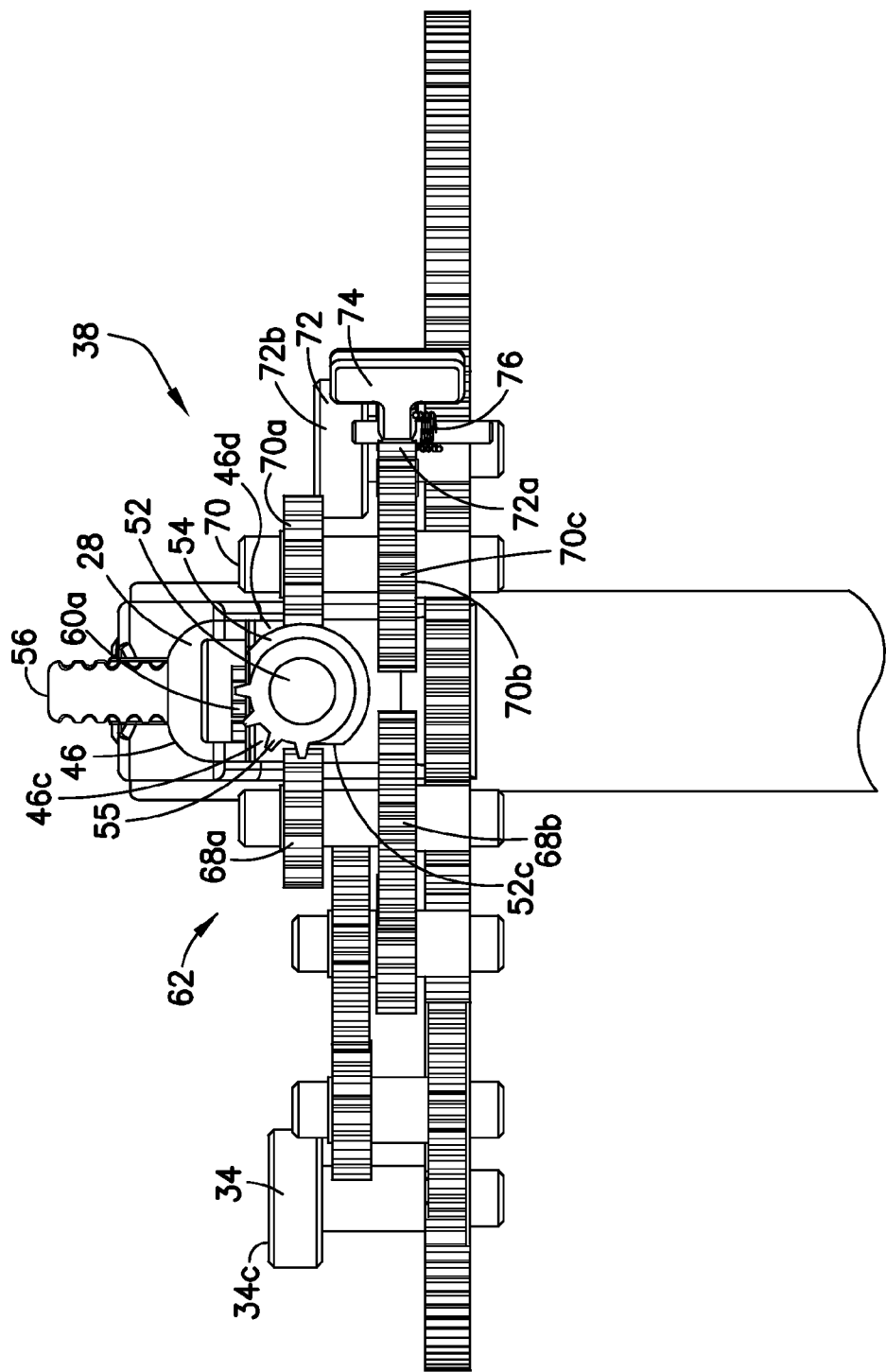
FIG. 10 is a further partial side view of the retractor gearing mechanism shown in FIG. 9 with the switch in the second position of FIG. 8

Referring still to FIGS. 4 and 6 and with additional reference to FIGS. 8-10, elements of the clutch mechanism 36 are described. The housing 46 of each arm 28 movably supports therein an elongate bar such as an elongate shaft 52. Shaft 52 in this particular arrangement is generally circular and is supported for rotation about its longitudinal axis 52a within housing 46. A series of linearly arranged gear teeth 54 is provided lengthwise along the periphery of shaft 52 at least over a radial portion 52b of the shaft 52 as depicted in FIG. 4. Another series of gear teeth 55 (See FIGS. 9 and 10) is arranged arcuately around a portion of the periphery of shaft 52, the function of which will be described hereinbelow. The radial portion 52c of the shaft 52 without gear teeth 54 along its length is illustrated in FIG. 8. In this particular arrangement, the teeth 54 extend over a radial portion 52b of about 90°, it being understood that the radial extent having teeth 54 may vary, provided there is both a longitudinal extent with teeth 54 and a longitudinal extent without teeth. Still referring to FIGS. 4 and 6, a switch 56 is rotatably supported by housing 46. Switch 56 comprises a rotatable knob 58 that is attached to a switch gear 60 for joint rotation therewith. Switch gear 60 includes a plurality of gear teeth 60a that are in engagement with teeth 55 on shaft 52. Thus, in a first position as shown in FIGS. 4 and 9, teeth 54 are arranged to be exposed through a window 46c of housing 46 with knob 58 in a first orientation and gear teeth 60a are in engagement with gear teeth 55 on shaft 52. Rotation of the knob 58 approximately 180° to the orientation shown in FIGS. 8 and 10 rotates the switch gear 60 which in turn through engagement of teeth 60a with teeth 55 rotates shaft 52 about axis 52a approximately 90° to a second position until the portion 52c of the shaft 52 without gears is exposed through window 46c. Through such rotation of shaft 52 the arm 28 may be selectively engaged with the main gear 32 as part of the clutch mechanism 36. As will be described, the teeth 54 on the shaft 52 effectively function as a rack to convert the rotary motion of the main gear 32 into linear motion for translating the arm 28 relative to the ring member 22 through the clutch mechanism 36.

Referring again to FIG. 3 and also to FIG. 9, further details of the clutch mechanism 36 are described. In the particular arrangement being described, clutch mechanism 36 includes a coupling gear mechanism 62 comprising three step gears 64, 66 and 68 all of which are in engagement with each other. The step gears 64, 66 and 68 are used in the coupling gear mechanism 62 so as to provide a desired gear reduction between the rate at which main gear 32 rotates and the rate at which each arm 28 translates relative to ring member 22. As such, coupling gear mechanism 62 may allow an arm 28 to translate at 1 mm increments for each one quarter turn of actuator 34. Step gear 64 comprises an upper smaller gear 64a and a lower larger gear 64b. Larger gear 64b has gear teeth in engagement with the gear teeth 32a of main gear 32 and as such when main gear 32 rotates it will rotate larger gear 64b. Step gear 66 comprises an upper larger gear 66a and a lower smaller gear 66b. Larger gear 66a has gear teeth in engagement with gear teeth on smaller gear 64a of step gear 64. Step gear 68 comprises an upper smaller gear 68a and a lower larger gear 68b. Larger gear 68b has gear teeth in engagement with gear teeth on smaller gear 66b of step gear 66. Rotation of the actuator 34 will effectively rotate the main gear 32 by the drive gear 34a with each of the step gears 64, 66 and 68 being rotated as a result of engagement of step gear 64 with the main gear 32. Smaller gear 68a of step gear 68 is positioned on ring member 22 adjacent arm 28 so that the gear teeth thereon will be engageable with the teeth 54 on shaft 52 which are exposed through window 46c of housing 46.

As illustrated in FIG. 9, shaft 52 is in the first position described with respect to FIG. 4 wherein gear teeth 54 on shaft 52 engage the teeth of smaller gear 68a. Teeth 55 are disposed on shaft 52 such that they do not make engagement with either the coupling gear mechanism 62 or the locking gear mechanism. When switch 56 has been actuated to place shaft 52 in such first position rotation of smaller gear 68a will linearly move shaft 52 through engagement with teeth 54 thereby translating arm 28 radially with respect to ring member 22. Smaller gear 68a will effectively serve as the pinion to convert rotary motion of the coupling gear mechanism 62 into linear motion by engagement with teeth 54 on shaft 52 which, as described hereinabove, serves as a rack. It should be understood, however, that while coupling gear mechanism 62 comprises three step gears 64, 66 and 68 in the particular arrangement being described, other gear mechanisms or a single coupling member may be used in the retractor 10. For example, a single coupling member may be defined by a single coupling gear with gear teeth with such single gear being disposed on ring member 22 and such that the gear teeth thereon are in engagement with gear teeth 32a on main gear 32 and are engageable with teeth 54 on shaft 52.

Referring still to FIG. 3 and again to FIG. 10, details of the locking mechanism 38 are described. In FIG. 10, shaft 52 has been rotated by switch 56 to the second position as illustrated in FIG. 8. During rotation of switch 56, switch gear 60 has likewise been rotated causing gear teeth 60a thereon through engagement with teeth 55 to have rotated shaft 52 about its axis 52a to the second position. In this second position, the radial portion 52c of the shaft 52 without teeth 54 is exposed through window 46c. As such, any rotation of smaller gear 68a through rotation of main gear 32 will not cause any translation of arm 28. In this position, teeth 54 on shaft 52 are exposed through a window 46d formed through the housing 46 opposite window 46c with the teeth 54 being engageable with the locking mechanism 38. Locking mechanism 38 comprises a locking gear 70 and an override gear 72. Locking gear 70 is a step gear that comprises an upper smaller gear 70a and a lower larger gear 70b. Smaller gear 70a has teeth engageable with teeth 54 on shaft 52 when shaft 52 is in the second position, as illustrated in FIG. 10. Override gear 72 comprises a gear 72a having gear teeth in engagement with the gear teeth on larger gear 70b. A pawl 74 is supported on ring member 22 adjacent locking gear 70, the pawl 74 being spring-loaded by a spring element such as a torsion spring 76. Teeth 70c on larger gear 70b are formed as ratchet teeth such that when teeth 70c are in engagement with pawl 74 locking gear 70 can only rotate in one direction is indicated by arrow 78 in FIG. 3. As such, in the second position of shaft 52 as shown in FIG. 10, wherein teeth 54 are in engagement with the gear teeth of smaller gear 70a, arm 28 is prevented from translating radially inwardly relative to ring member 22. Release of the pawl 76 from the gear teeth 70c on larger gear 70b will allow free rotation of locking gear 70 whereby arm 28 may be freely and manually translatable.

Figure 11:
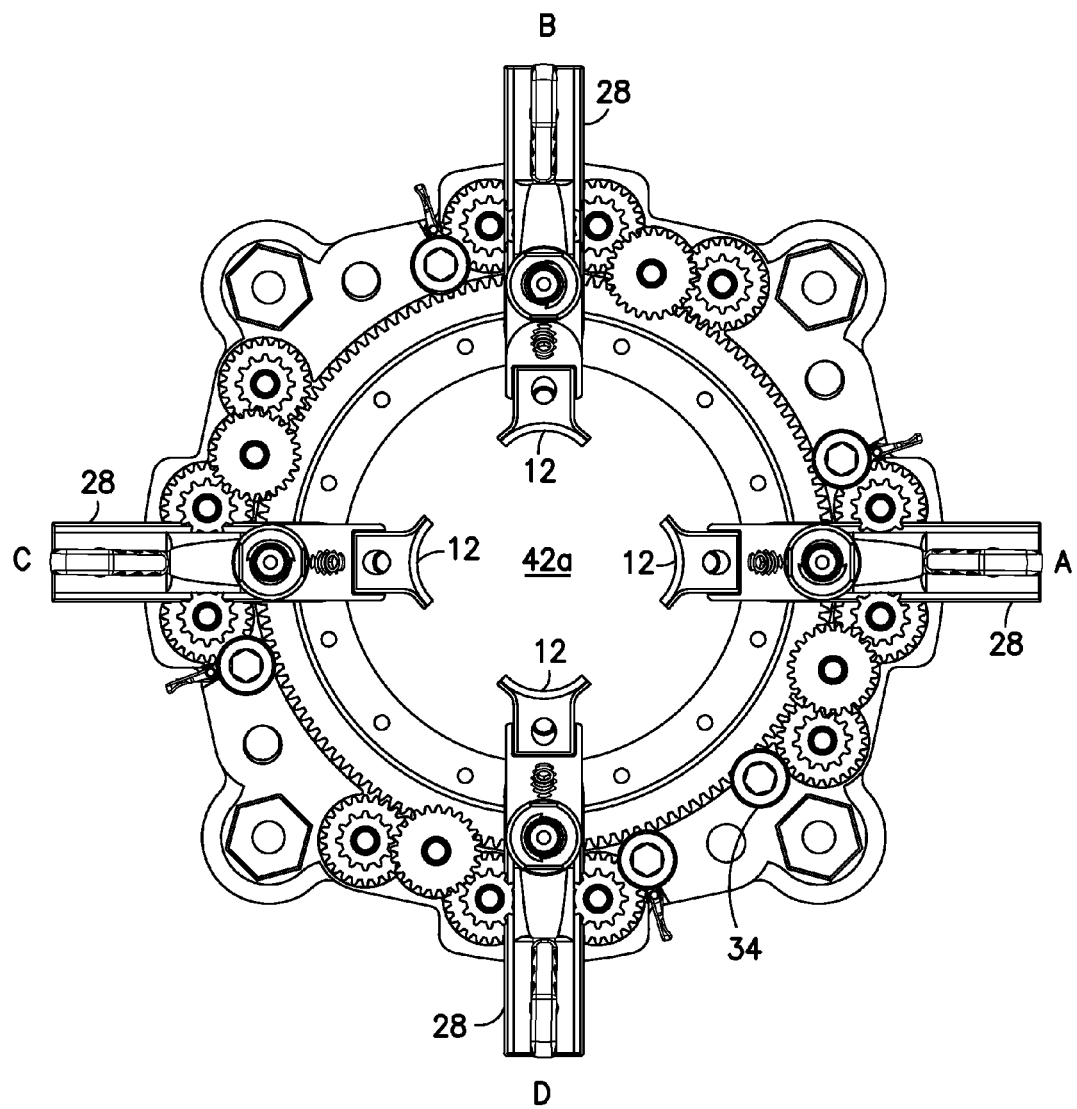
FIG. 11 is a further top plan view of the retractor shown in FIG. 3 with all the translatable arms and blades supported thereon having been translated radially outwardly to expand the surgical corridor.

With pawl 76 still in engagement with gear teeth 70c on larger gear 70b arm 28, while being prevented from translating radially inwardly, may be independently translated radially outwardly upon rotation of override gear 72. Override gear 72 comprises an upper portion 72b having an engagement surface such as a hex configuration for engagement with a complementary surface on a suitable instrument (not shown) for rotating override gear 72. Rotation of override gear 72 causes gear 72a to rotate locking gear 70 through engagement with larger gear 70b. With the gear teeth on smaller gear 70a being in engagement with teeth 54 on shaft 52, shaft 52 translates radially outwardly upon rotation of smaller gear 70a. Pawl 76 will prevent translation of shaft 52 radially inwardly. While the teeth 54 on shaft 52 are shown in FIGS. 10 and 11 as extending over a radial extent to engage gear mechanism 62 in the first position and the locking mechanism 38 in the second position, teeth 54 may be configured on shaft 52 to extend over a radial extent to engage both the coupling gear mechanism 62 and the locking mechanism 38 when the shaft 52 is being rotated from the first position to the second position. Such a construction would substantially prevent arm 28 from radially slipping during the transition between the first to the second position.

Having described the details of the retractor 10, further aspects of the construction of the retractor 10 are described. For example, in the arrangement for use in spinal surgery particularly from the lateral approach, the retractor frame 14 may have a maximum outer diameter of about 5.26 inches. As such, the retractor 10 will be relatively easy to handle by a surgeon, will present a relatively small footprint and generally fit between a patient's iliac crest and ribs during surgery. For this application, all the components of the retractor 10 may be formed of aluminum except for the gears which would be formed of stainless steel. The aluminum components are desirable for not only their strength and rigidity but also for use with fluoroscopic imaging whereby the aluminum material is not fully opaque but allows a degree of translucency to aid fluoroscopic visibility for the surgeon.

During use of the retractor 10 in this particular arrangement, a surgeon forms an initial incision through the tissue of the patient from the lateral aspect in a manner to create a surgical corridor through the psoas muscle down to a surgical site adjacent the lateral surface of a spinal disc. The initial incision may be dilated by a series of sequentially larger dilation cannulas as is conventionally known in the art to further expand the incision. Detection of nerves during the dilation process may be performed as is known in the art by conventional neural monitoring techniques. Suitable dilation and neural monitoring techniques are described, for example, in commonly assigned PCT Application Number PCT/US 12/54051, entitled "Apparatus for Dilating Bodily Tissue and for Monitoring Neural Activity in the Dilated Bodily Tissue", filed Sep. 7, 2012, and published as WO 2013/036705A1 on Mar. 14, 2013, this PCT Application being incorporated herein by reference in its entirety.

After suitable dilation and nerve detection, the surgeon will determine the depth of the corridor and the length of blades 12 to be used in retractor 10. A kit may be provided with a set of different length blades 12, together with various other instruments and tools for use during surgery. The length of blades 12 may range from 9 cm-17 cm. Once the proper length is determined, the surgeon will select a set of four retractor members 41 having blades 12 of any desired length and attach one retractor member 41 to each arm 28 of the retractor 10 as described hereinabove. The retractor members 41 on arms 28 will be adjusted to an initial position as depicted in FIG. 3 wherein the distal ends of the blades 12 form the substantially enclosed opening 42. As used herein, a substantially enclosed opening means an opening wherein the longitudinal edges of each of the blades 12 are in contact or a substantially small space exists between each of the blades 12 along their lengths. The opening 42 is formed so that the blades 12 simultaneously slide over the largest of the sequential dilation cannulas in a relatively close sliding fit. In some instances the blades 12 may be formed to have an arcuate extent less than the arcuate extent of the blades supports 43, as seen in FIG. 4. As such, the side edges of the blade supports 43 may be in contact as the retractor 10 is positioned over the largest dilation cannula with a small gap between the longitudinal edges of the blades along the lengths. For this particular application, the initial opening 42 may range from 13 mm-18 mm, although different opening configurations and positions may be achieved.

After the blades 12 are inserted into the incision over the largest dilation cannula, the retractor 10 is rigidly secured to the operating table by bracket 20. Bracket 20 as shown in FIGS. 1-2 is generally horse-shoe shaped with a pair of arms 20a and 20b each terminating with a thumbscrew 80 and 82. Thumbscrew 80 terminates in a threaded portion 80a for threaded engagement in a threaded hole 40a in one mounting portion 40 and thumbscrew 82 terminates in a threaded portion 82a for threaded engagement in threaded hole 40a in a second mounting portion 40. The distal ends of each mounting bracket arm 20a and 20b may be configured to have a polygonal shape to match a complementary polygonal shape in each mounting portion 40 so as to provide a secure, rigid connection between the retractor frame 14 and the bracket 20. Bracket 20 includes a mounting portion 20c at the base of the bracket 20 formed similarly to mounting portions 40 for secure connection thereto to a rigid mounting arm which in turn is connected to the operating table. While it should be appreciated that an individual mounting portion 40 on the retractor frame 14 may be used to attach the retractor 10 to the operating table via a rigid mounting arm, use of the bracket 20 which attaches to at least two mounting portions 40 on the retractor 10 provides a more stable, rigid connection.

With the retractor 10 rigidly connected to the operating table in a manner to maintain the position of the retractor stable during the surgical procedure, the dilation cannulas may be removed from the incision. The surgeon may now select which quadrants of the opening 42 may be expanded. For example, if the surgeon wishes to expand the incision in all of the quadrants A, B, C and D, switch 56 on all of the housings 46 would be rotated to the first position as depicted in FIG. 4. With a suitable tool the surgeon will rotate actuator 34 which will rotate main gear 32 and through the clutch mechanism 36 all arms 28 will translate radially outwardly upon rotation of the actuator 34, expanding the initial opening 42 equally in all directions to the expanded opening 42a as shown in FIG. 11. The initial opening 42 may be increased to an expanded opening 42a in the range of 14 mm-36 mm, although other suitable ranges are contemplated based upon the application. Smaller expansion may be desirable wherein an implant is inserted through the expanded opening to the surgical site, such as in the intradiscal space, while a larger expansion may be desired when additional surgical procedures, such as subsequent grafting around the implant are performed through the retractor. Any or all of the distal ends 12b may be further expanded radially outwardly in a toeing manner as described hereinabove with respect to FIG. 7. Suitable illuminating elements may be used in conjunction with one or more retractor members 41 as described hereinabove either before or after blades 12 are radially expanded or toed.

Figure 12:
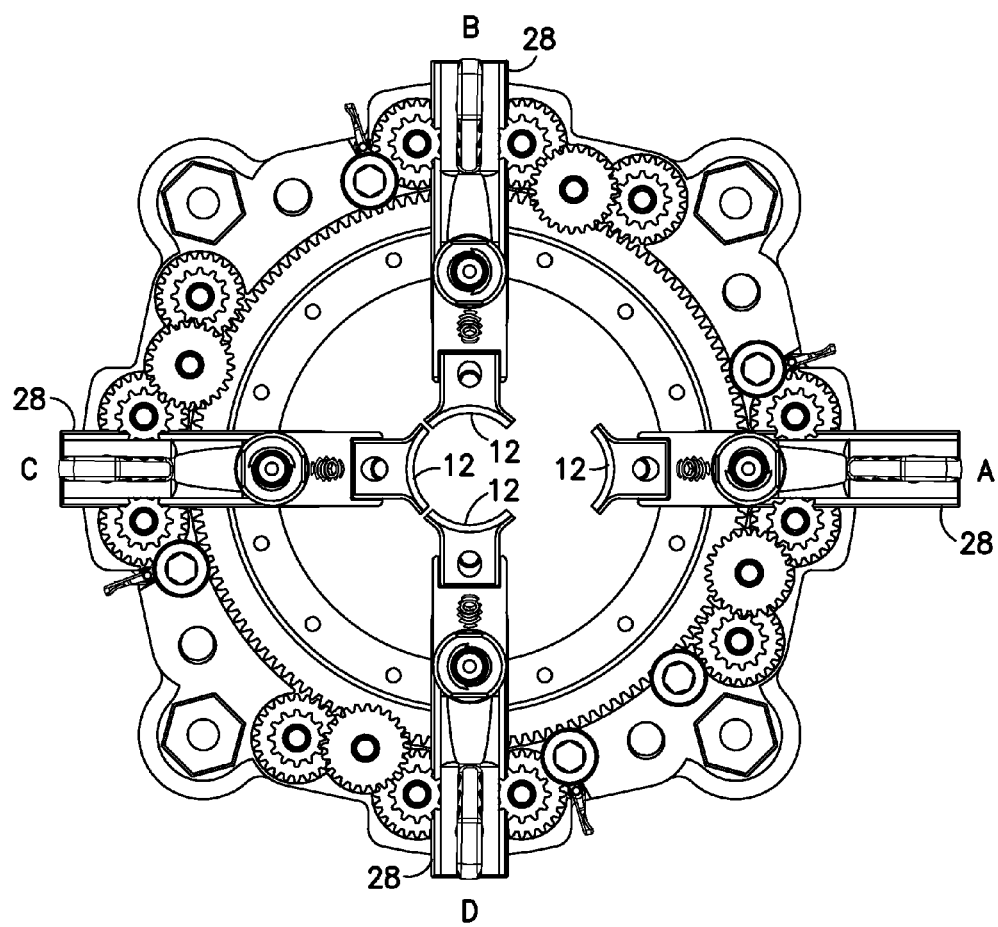
FIG. 12 is a further top plan view of the retractor shown in FIG. 3 with one of the translatable arms and blade supported thereon having been translated radially outwardly to expand the surgical corridor in a selected direction.

In certain situations, the surgeon may wish to radially expand the dilated incision in only one direction, such as in quadrant A. In this procedure, the surgeon would position switch 56 on arm 28 in quadrant A in the first position while moving switch 56 on the remaining arms 28 in quadrants B, C and D to the second position. Rotation of the actuator by the suitable tool rotates main gear 32 and with only arm 28 in quadrant A being selectively engaged with main gear 32 through its associated clutch mechanism 36, only this arm 28 will translate radially outwardly as shown in FIG. 12. As such, a surgeon may selectively translate any one or all of the arms 28 or any combination of arms 28 in the use of retractor 10 in one or more selected desired directions from a single source, such as actuator 34.

Figure 13:
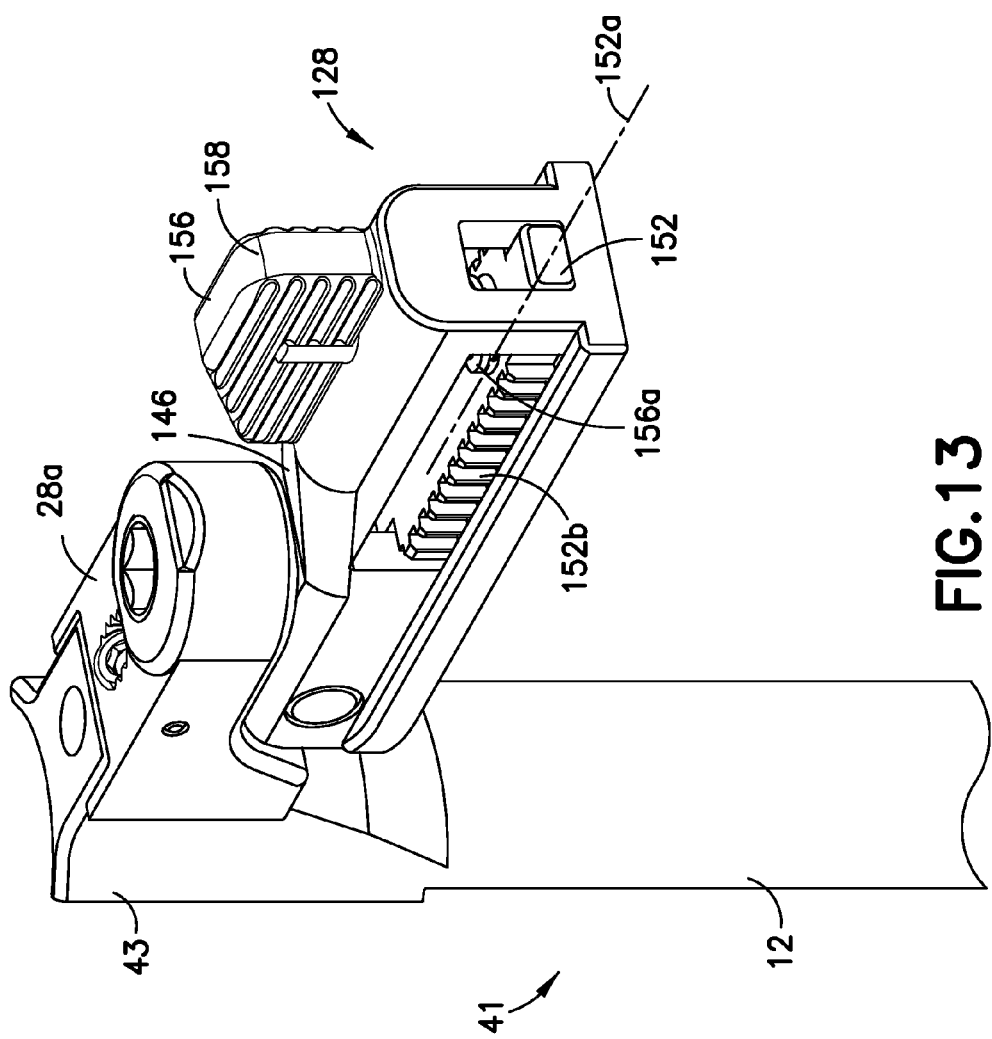
FIG. 13 is a top perspective view of an alternative translatable arm with a retractor member supported thereon and a switch oriented in a first position.
Figure 14:
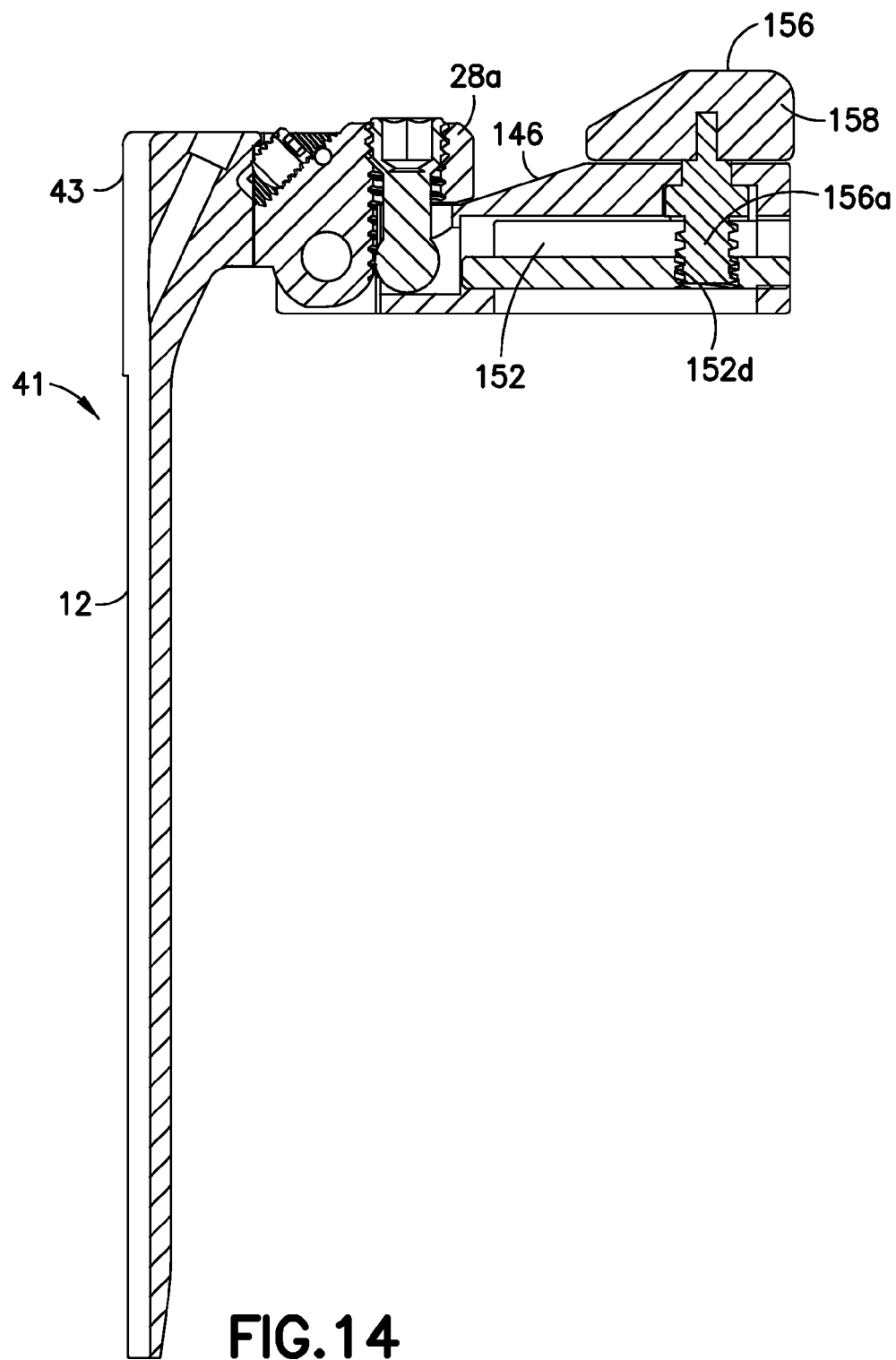
FIG. 14 is a cross-sectional view of the alternative arm arrangement of FIG. 13.
Figure 15:
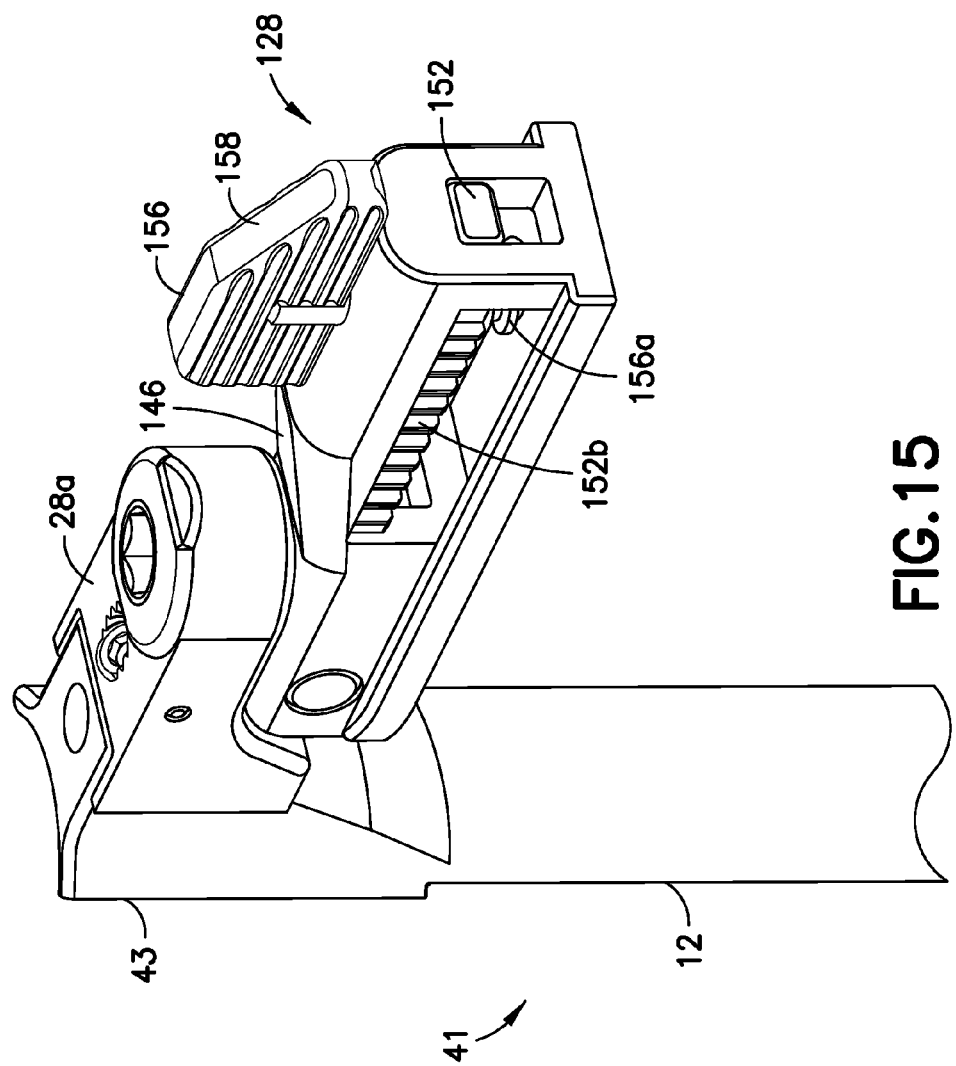
FIG. 15 is a top perspective view of the alternative arm arrangement of FIG. 13, with the switch oriented in a second position.
Figure 16:
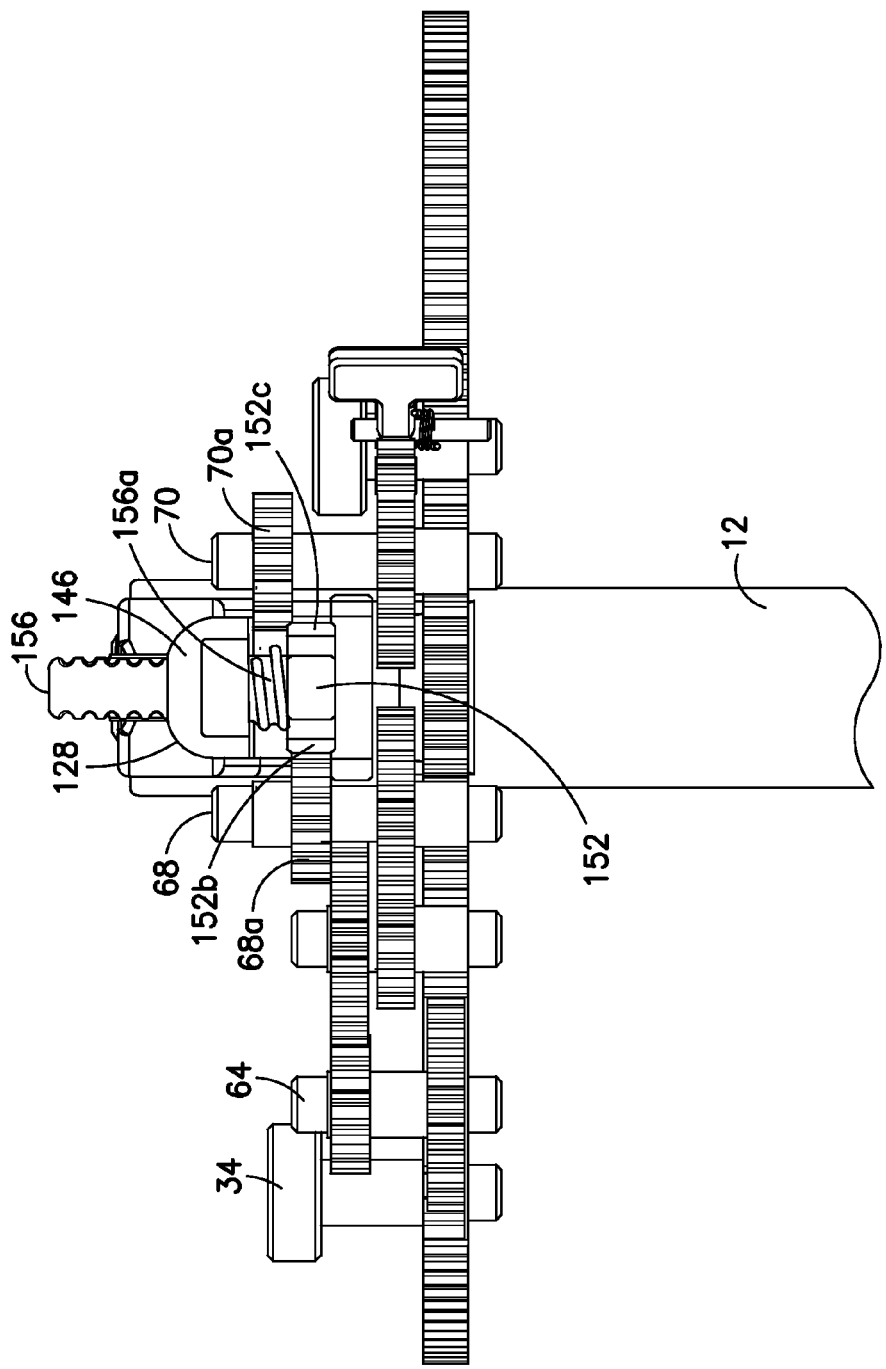
FIG. 16 is a partial side view of the retractor of FIG. 3 as viewed along the direction line IX in FIG. 3 with a portion of the retractor frame removed to reveal only the gearing mechanism in one quadrant used with the alternative arm arrangement of FIG. 13 with the switch in the first position of FIG. 13.

Having described a particular arrangement of retractor 10, it should be understood that variations may be made thereto within the contemplated scope of the invention. For example, as an alternative to movable bar being a rotatable shaft 52, the movable bar may be provided to selectively move linearly between the first position and a second position described hereinabove. As illustrated in FIGS. 13-17, a bar 152 supported in a modified arm 128 having a housing 146 is movable in a transverse direction from the first position to the second position, as will be described. Bar 152 is elongate and generally rectangular defining a longitudinal axis 152a. Gear teeth 154b are linearly disposed on one lateral side of bar 152 that faces smaller gear 68a of the coupling gear mechanism 62. Similar gear teeth 152c are linearly disposed on the opposite lateral side of bar 152 that faces smaller gear 70a of the locking mechanism 38. Smaller gear 70a is arranged on ring member 22 at a different higher plane than smaller gear 68a, as seen in FIGS. 16 and 17. A switch 156 having a knob 158 is rotatably supported by housing 146, switch 156 having a threaded post 156a threadedly connected to a threaded opening 152d in bar 152. In FIGS. 13 and 16, the bar 152 and switch 156 are in the first position, and as seen in FIG. 16 gear teeth 154b are in engagement with smaller gear 68a. In this first position, gear teeth 152c do not engage smaller gear 70a. Rotation of switch 156 by knob 158 to the position illustrated in FIG. 15 rotates threaded post 156a causing bar 152 to elevate in a linear direction generally orthogonal to axis 152a to the second position. As seen in FIG. 17, in this second position gear teeth 152c are in engagement with smaller gear 70a while gear teeth 152b do not engage smaller gear 68a. In all other respects, the retractor with the alternative arm arrangement functions in the same manner as set forth regarding the embodiments previously described hereinabove.

It should also be appreciated that while the particular arrangement of retractor 10 has been described herein as a four bladed retractor, retractor 10 may be configured for use with as few as two blades or more than four. It should further be appreciated that while it is desirable in some instances for all of the blades to be independently translatable, there may be certain situations wherein a pair of blades 12, such as those in quadrants A and B are jointly engageable with main gear 32 through clutch mechanism 36 by movement of a single switch 56. In addition, there may be certain other applications wherein one or more blades of the retractor are fixed relative to frame 14 with at least one arm 28 and the blade supported thereon being selectively engageable with main gear 32 through clutch mechanism 36.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. Also, while the illustrated embodiments have been directed particularly to a retractor for use in spinal surgery, it should be understood that variations may be made to the retractor to enable use in the expansion of bodily tissue in other surgical procedures. Modifications in size may be necessary depending upon the bodily tissue to be retracted.

What is claimed is:

1. A method of retracting body tissue during spinal surgery, comprising the steps of:
    making an incision through body tissue of a patient to create a surgical corridor to a surgical site adjacent the surface of a spinal disc;
    placing a plurality of blades supported by a retractor simultaneously into said incision, each of said blades being selectively movable individually one at a time from a single source on said retractor or alternatively, jointly from said single source; and
    operating said single source to selectively move only one blade in one direction or more than one blade in a plurality of directions to expand said incision.

2. The method of claim 1, wherein said retractor comprises a frame defining a generally central interior space, a plurality of arms supported by said frame for selective independent radial translational movement thereon, each arm including a blade configured to extend into said interior space.

3. The method of claim 2, wherein each blade is selectively attachable to a respective arm.

4. The method of claim 2, wherein said retractor comprises a clutch mechanism supported by said frame and associated with each arm for engaging and disengaging each arm with said single source.

5. The method of claim 4, wherein said clutch mechanism comprises a switch associated with each arm, and wherein each of said arms is engaged or disengaged with said single source by individual operation of a respective switch.

6. The method of claim 1, wherein each of said plurality of blades is selectively individually engageable and disengageable with said single source.

7. The method of claim 6, wherein there are four blades.

8. The method of claim 7, wherein said single source is operated to move only one blade in said only one direction while the other three blades remain stationary.

9. The method of claim 7, wherein said single source is operated to move two blades each in different directions while the other two blades remain stationary.

10. The method of claim 7, wherein said single source is operated to move three blades each in different directions while the other blade remains stationary.

11. The method of claim 7, wherein said single source is operated to move all four blades each in different directions.

* * * * *